(12) United States Patent
Metzger et al.

(10) Patent No.: US 9,289,299 B2
(45) Date of Patent: Mar. 22, 2016

(54) METHOD AND APPARATUS FOR AUGUMENTING BONE DEFECTS

(71) Applicant: Biomet Manufacturing, LLC, Warsaw, IN (US)

(72) Inventors: Robert Metzger, Wakarusa, IN (US); Brian M. May, Warsaw, IN (US); Daniel E. Williamson, Warsaw, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 0 days.

(21) Appl. No.: 13/834,914

(22) Filed: Mar. 15, 2013

(65) Prior Publication Data

US 2013/0211536 A1    Aug. 15, 2013

Related U.S. Application Data

(62) Division of application No. 12/708,309, filed on Feb. 18, 2010, now Pat. No. 8,444,699.

(51) Int. Cl.
*A61F 2/28* (2006.01)
*A61F 2/30* (2006.01)
(Continued)

(52) U.S. Cl.
CPC .............. *A61F 2/28* (2013.01); *A61F 2/30734* (2013.01); *A61F 2/3607* (2013.01); *A61F 2/3662* (2013.01); *A61L 27/56* (2013.01); *A61F 2/30965* (2013.01); *A61F 2/3672* (2013.01); *A61F 2002/3021* (2013.01); *A61F 2002/30062* (2013.01); *A61F 2002/3092* (2013.01); *A61F 2002/3096* (2013.01); *A61F 2002/30217* (2013.01); *A61F 2002/30332* (2013.01); *A61F 2002/30342* (2013.01); *A61F 2002/30406* (2013.01); *A61F 2002/30487* (2013.01);
(Continued)

(58) Field of Classification Search
CPC . A61F 2/28; A61F 2/3859; A61F 2002/2817; A61F 2002/2842; A61F 2002/30011; A61F 2002/30062; A61F 2002/2835; A61F 2002/2839; A61F 2002/30004; A61F 2002/30006; A61F 2/30; A61F 2002/2825; A61F 2/30756; A61F 2002/30759; A61F 2002/30761; A61F 2002/30764; A61F 2/3872; A61F 2/3877
USPC .......... 623/22.46, 14.12, 23.71–23.76, 20.16, 623/23.28; 606/248, 249, 284, 285
See application file for complete search history.

(56) References Cited

U.S. PATENT DOCUMENTS 3,605,123 A    9/1971 Hahn
3,929,971 A    12/1975 Roy
(Continued)

OTHER PUBLICATIONS

"Artificial Bone Grafts:Pro Osteon", http://www.arthroscopy.com/sp12013.htm, Copyright 1999, 4 sheets.
(Continued)

*Primary Examiner* — Alvin Stewart
(74) *Attorney, Agent, or Firm* — Schwegman Lundberg & Woessner, P.A.

(57) ABSTRACT

A bone augment for repairing a bone defect and associated method. The bone augment includes a porous body and a reinforcement member. The porous body defines a plurality of pores and is configured to be intraoperatively shaped to correspond to the bone defect. The reinforcement member is mounted on an exterior surface of the porous body and is configured to be intraoperatively shaped to correspond to the bone defect.

19 Claims, 8 Drawing Sheets

(51) Int. Cl.
*A61F 2/36* (2006.01)
*A61L 27/56* (2006.01)

(52) U.S. Cl.
CPC ............... *A61F2002/30578* (2013.01); *A61F 2002/30738* (2013.01); *A61F 2310/00341* (2013.01); *A61L 2430/02* (2013.01)

(56) References Cited

U.S. PATENT DOCUMENTS

| | | | | |
|---|---|---|---|---|
| 4,202,055 | A | 5/1980 | Reiner et al. | |
| 4,502,161 | A * | 3/1985 | Wall | 623/14.12 |
| 4,599,086 | A * | 7/1986 | Doty | 606/86 A |
| 4,655,777 | A | 4/1987 | Dunn et al. | |
| 4,722,870 | A | 2/1988 | White | |
| 4,737,411 | A | 4/1988 | Graves, Jr. et al. | |
| 4,769,011 | A | 9/1988 | Swaniger | |
| 4,822,366 | A | 4/1989 | Bolesky | |
| 4,846,839 | A | 7/1989 | Noiles | |
| 4,861,733 | A | 8/1989 | White | |
| 4,892,545 | A * | 1/1990 | Day et al. | 623/17.11 |
| 4,944,757 | A | 7/1990 | Martinez et al. | |
| 4,969,896 | A | 11/1990 | Shors | |
| 4,976,736 | A | 12/1990 | White et al. | |
| 5,002,578 | A | 3/1991 | Luman | |
| 5,084,051 | A | 1/1992 | Tormala et al. | |
| 5,137,535 | A | 8/1992 | Keller | |
| 5,152,791 | A * | 10/1992 | Hakamatsuka et al. | 623/23.56 |
| 5,181,928 | A | 1/1993 | Bolesky et al. | |
| 5,186,162 | A | 2/1993 | Talish et al. | |
| 5,211,160 | A | 5/1993 | Talish et al. | |
| 5,290,313 | A | 3/1994 | Heldreth | |
| 5,306,311 | A * | 4/1994 | Stone et al. | 623/14.12 |
| 5,348,788 | A | 9/1994 | White | |
| 5,455,100 | A | 10/1995 | White | |
| 5,487,933 | A | 1/1996 | White | |
| 5,552,454 | A | 9/1996 | Kretschmann et al. | |
| 5,571,193 | A | 11/1996 | Kampner | |
| 5,607,474 | A * | 3/1997 | Athanasiou et al. | 623/23.71 |
| 5,620,448 | A * | 4/1997 | Puddu | 606/87 |
| 5,653,765 | A | 8/1997 | McTighe et al. | |
| 5,725,592 | A | 3/1998 | White et al. | |
| 5,728,510 | A | 3/1998 | White | |
| 5,766,251 | A * | 6/1998 | Koshino | 623/11.11 |
| 5,824,088 | A * | 10/1998 | Kirsch | 424/423 |
| 5,876,452 | A * | 3/1999 | Athanasiou et al. | 623/23.72 |
| 5,876,459 | A | 3/1999 | Powell | |
| 5,879,391 | A | 3/1999 | Slamin | |
| 5,879,394 | A | 3/1999 | Ashby et al. | |
| 5,902,340 | A | 5/1999 | White et al. | |
| 5,904,717 | A * | 5/1999 | Brekke et al. | 424/423 |
| 5,906,644 | A | 5/1999 | Powell | |
| 5,910,172 | A | 6/1999 | Penenberg | |
| 5,931,871 | A | 8/1999 | Baur et al. | |
| 5,976,188 | A | 11/1999 | Dextradeur et al. | |
| 5,977,204 | A | 11/1999 | Boyan et al. | |
| 5,986,169 | A | 11/1999 | Gjunter | |
| 6,008,430 | A | 12/1999 | White | |
| 6,008,433 | A * | 12/1999 | Stone | 623/20.14 |
| 6,013,853 | A * | 1/2000 | Athanasiou et al. | 424/423 |
| 6,066,175 | A * | 5/2000 | Henderson et al. | 623/17.11 |
| 6,080,194 | A * | 6/2000 | Pachence et al. | 623/23.76 |
| 6,086,593 | A * | 7/2000 | Bonutti | 606/87 |
| 6,093,205 | A * | 7/2000 | McLeod et al. | 623/17.16 |
| 6,120,503 | A * | 9/2000 | Michelson | 606/86 A |
| 6,156,037 | A * | 12/2000 | LeHuec et al. | 606/247 |
| 6,156,070 | A | 12/2000 | Incavo et al. | |
| 6,187,329 | B1 * | 2/2001 | Agrawal et al. | 424/426 |
| 6,200,347 | B1 * | 3/2001 | Anderson et al. | 623/16.11 |
| 6,203,546 | B1 * | 3/2001 | MacMahon | 606/87 |
| 6,206,922 | B1 * | 3/2001 | Zdeblick et al. | 623/17.11 |
| 6,224,602 | B1 | 5/2001 | Hayes | |
| 6,235,059 | B1 * | 5/2001 | Benezech et al. | 623/17.16 |
| 6,264,698 | B1 * | 7/2001 | Lawes et al. | 623/22.12 |
| 6,264,699 | B1 | 7/2001 | Noiles et al. | |
| 6,270,502 | B1 | 8/2001 | Stulberg | |
| 6,296,667 | B1 | 10/2001 | Johnson et al. | |
| 6,302,888 | B1 | 10/2001 | Mellinger et al. | |
| 6,309,395 | B1 | 10/2001 | Smith et al. | |
| 6,319,286 | B1 | 11/2001 | Fernandez et al. | |
| 6,342,157 | B1 | 1/2002 | Hood, III | |
| 6,344,496 | B1 | 2/2002 | Niederauer et al. | |
| 6,350,284 | B1 * | 2/2002 | Tormala et al. | 623/17.19 |
| 6,364,881 | B1 | 4/2002 | Apgar et al. | |
| 6,365,149 | B2 * | 4/2002 | Vyakarnam et al. | 424/93.1 |
| 6,376,573 | B1 | 4/2002 | White et al. | |
| 6,383,221 | B1 * | 5/2002 | Scarborough et al. | 623/17.11 |
| 6,454,811 | B1 * | 9/2002 | Sherwood et al. | 623/23.76 |
| 6,464,728 | B1 | 10/2002 | Murray | |
| 6,518,328 | B2 | 2/2003 | Kumar | |
| 6,520,994 | B2 | 2/2003 | Nogarin | |
| 6,524,342 | B1 | 2/2003 | Muhlhausler et al. | |
| 6,524,345 | B1 | 2/2003 | Valimaa et al. | |
| 6,527,810 | B2 | 3/2003 | Johnson et al. | |
| 6,562,073 | B2 * | 5/2003 | Foley | 623/17.11 |
| 6,565,884 | B2 | 5/2003 | Nimni | |
| 6,575,982 | B1 * | 6/2003 | Bonutti | 606/90 |
| 6,576,017 | B2 * | 6/2003 | Foley et al. | 623/17.16 |
| 6,626,945 | B2 * | 9/2003 | Simon et al. | 623/17.19 |
| 6,626,950 | B2 * | 9/2003 | Brown et al. | 623/23.72 |
| 6,632,246 | B1 * | 10/2003 | Simon et al. | 623/14.12 |
| 6,632,247 | B2 | 10/2003 | Boyer, II et al. | |
| 6,635,087 | B2 * | 10/2003 | Angelucci et al. | 623/17.11 |
| 6,699,252 | B2 * | 3/2004 | Farr et al. | 606/79 |
| 6,706,072 | B2 | 3/2004 | Dwyer et al. | |
| 6,716,250 | B2 | 4/2004 | Ganjianpour | |
| 6,723,129 | B2 | 4/2004 | Dwyer et al. | |
| 6,843,805 | B2 * | 1/2005 | Webb et al. | 623/17.16 |
| 6,843,808 | B2 | 1/2005 | Grundei | |
| 6,858,042 | B2 * | 2/2005 | Nadler et al. | 623/11.11 |
| 6,869,450 | B2 | 3/2005 | Grundei | |
| 6,875,239 | B2 | 4/2005 | Gerbec et al. | |
| 6,887,276 | B2 | 5/2005 | Gerbec et al. | |
| 6,981,991 | B2 | 1/2006 | Ferree | |
| 6,989,034 | B2 * | 1/2006 | Hammer et al. | 623/23.72 |
| 7,018,420 | B2 | 3/2006 | Grundei | |
| 7,097,664 | B2 | 8/2006 | Despres, III et al. | |
| 7,105,026 | B2 | 9/2006 | Johnson et al. | |
| 7,122,056 | B2 | 10/2006 | Dwyer et al. | |
| 7,122,057 | B2 * | 10/2006 | Beam et al. | 623/23.51 |
| 7,156,880 | B2 | 1/2007 | Evans et al. | |
| 7,166,133 | B2 | 1/2007 | Evans et al. | |
| 7,175,664 | B1 | 2/2007 | Lakin | |
| 7,189,263 | B2 | 3/2007 | Erbe et al. | |
| 7,192,448 | B2 | 3/2007 | Ferree | |
| 7,291,169 | B2 * | 11/2007 | Hodorek | 623/14.12 |
| 7,427,293 | B2 * | 9/2008 | Nycz et al. | 623/14.12 |
| 7,431,874 | B2 | 10/2008 | Muratoglu et al. | |
| 7,435,263 | B2 | 10/2008 | Barnett et al. | |
| 7,445,639 | B2 | 11/2008 | Metzger et al. | |
| 7,470,289 | B2 | 12/2008 | Brehm | |
| 7,497,874 | B1 | 3/2009 | Metzger et al. | |
| 7,531,000 | B2 * | 5/2009 | Hodorek | 623/14.12 |
| 7,572,291 | B2 * | 8/2009 | Gil et al. | 623/14.12 |
| 7,582,092 | B2 | 9/2009 | Jones et al. | |
| 7,682,540 | B2 * | 3/2010 | Boyan et al. | 264/212 |
| 7,691,114 | B1 * | 4/2010 | Duche | 606/152 |
| 7,691,150 | B2 | 4/2010 | Cronin et al. | |
| 7,740,662 | B2 | 6/2010 | Barnett et al. | |
| 7,758,643 | B2 * | 7/2010 | Stone et al. | 623/14.12 |
| 7,780,708 | B2 * | 8/2010 | Morris et al. | 606/279 |
| 7,794,503 | B2 | 9/2010 | Daniels et al. | |
| 7,806,911 | B2 * | 10/2010 | Peckham | 606/248 |
| 7,819,918 | B2 * | 10/2010 | Malaviya et al. | 623/14.12 |
| 7,833,245 | B2 * | 11/2010 | Kaes et al. | 606/246 |
| 7,854,737 | B2 | 12/2010 | Daniels et al. | |
| 7,857,858 | B2 | 12/2010 | Justin et al. | |
| 7,879,100 | B2 * | 2/2011 | Denoziere et al. | 623/17.11 |
| 7,892,261 | B2 * | 2/2011 | Bonutti | 606/279 |
| 7,892,291 | B2 * | 2/2011 | Evans et al. | 623/23.51 |
| 7,909,883 | B2 | 3/2011 | Sidebotham | |
| 7,951,205 | B2 | 5/2011 | McCleary et al. | |
| 7,972,380 | B2 * | 7/2011 | Linares | 623/14.12 |
| 8,012,205 | B2 * | 9/2011 | Plouhar et al. | 623/13.17 |

(56) References Cited

U.S. PATENT DOCUMENTS

| | | | |
|---|---|---|---|
| 8,083,749 B2 * | 12/2011 | Taber | 606/96 |
| 8,100,982 B2 | 1/2012 | Heck et al. | |
| 8,133,421 B2 * | 3/2012 | Boyce et al. | 264/109 |
| 8,142,502 B2 * | 3/2012 | Stone et al. | 623/14.12 |
| 8,163,028 B2 | 4/2012 | Metzger et al. | |
| 8,187,326 B2 * | 5/2012 | Hammer et al. | 623/16.11 |
| 8,231,685 B2 * | 7/2012 | Fritz et al. | 623/23.57 |
| 8,241,293 B2 * | 8/2012 | Stone et al. | 606/87 |
| 8,241,367 B2 | 8/2012 | Justin et al. | |
| 8,257,444 B2 * | 9/2012 | Linares | 623/18.11 |
| RE43,714 E * | 10/2012 | Nadler et al. | 623/11.11 |
| 8,323,543 B2 * | 12/2012 | Michelson | 264/162 |
| 8,444,699 B2 | 5/2013 | Metzger et al. | |
| 8,480,757 B2 * | 7/2013 | Gage et al. | 623/23.55 |
| 8,592,531 B2 * | 11/2013 | Thomas et al. | 525/471 |
| 8,641,775 B2 * | 2/2014 | Harmon et al. | 623/23.72 |
| 8,652,214 B2 * | 2/2014 | Fritz et al. | 623/23.57 |
| 8,753,391 B2 * | 6/2014 | Lu et al. | 623/13.11 |
| 8,753,392 B2 * | 6/2014 | Melvin et al. | 623/13.14 |
| 8,764,830 B2 * | 7/2014 | Robinson et al. | 623/14.12 |
| 8,771,353 B2 * | 7/2014 | Gedet et al. | 623/14.12 |
| 8,771,363 B2 * | 7/2014 | Grotz | 623/20.21 |
| 8,834,568 B2 * | 9/2014 | Shapiro | 623/14.12 |
| 8,864,826 B2 * | 10/2014 | Pressacco | 623/11.11 |
| 2001/0039455 A1 * | 11/2001 | Simon et al. | 623/23.51 |
| 2002/0004685 A1 | 1/2002 | White | |
| 2002/0029084 A1 * | 3/2002 | Paul et al. | 623/23.63 |
| 2002/0065558 A1 * | 5/2002 | Varga et al. | 623/17.11 |
| 2002/0107571 A1 * | 8/2002 | Foley | 623/17.11 |
| 2002/0107572 A1 * | 8/2002 | Foley et al. | 623/17.11 |
| 2002/0119177 A1 * | 8/2002 | Bowman et al. | 424/423 |
| 2002/0123750 A1 * | 9/2002 | Eisermann et al. | 606/69 |
| 2002/0143403 A1 | 10/2002 | Vaidyanathan et al. | |
| 2002/0183845 A1 * | 12/2002 | Mansmann | 623/13.11 |
| 2003/0065397 A1 | 4/2003 | Hanssen et al. | |
| 2003/0105526 A1 * | 6/2003 | Bryant et al. | 623/16.11 |
| 2003/0109878 A1 | 6/2003 | Grundei | |
| 2003/0125740 A1 * | 7/2003 | Khanna | 606/61 |
| 2003/0139818 A1 | 7/2003 | Rogers et al. | |
| 2003/0167092 A1 * | 9/2003 | Foley | 623/17.11 |
| 2003/0195632 A1 * | 10/2003 | Foley et al. | 623/17.16 |
| 2004/0030388 A1 * | 2/2004 | Null et al. | 623/17.11 |
| 2004/0034419 A1 * | 2/2004 | Carter et al. | 623/14.12 |
| 2004/0059416 A1 * | 3/2004 | Murray et al. | 623/13.15 |
| 2004/0111161 A1 * | 6/2004 | Trieu | 623/17.16 |
| 2004/0162619 A1 | 8/2004 | Blaylock et al. | |
| 2004/0210222 A1 * | 10/2004 | Angelucci et al. | 606/69 |
| 2004/0243248 A1 | 12/2004 | Despres et al. | |
| 2004/0254646 A1 | 12/2004 | Stone et al. | |
| 2005/0010304 A1 | 1/2005 | Jamali | |
| 2005/0015088 A1 * | 1/2005 | Ringeisen | 606/69 |
| 2005/0075641 A1 * | 4/2005 | Singhatat et al. | 606/86 |
| 2005/0090900 A1 * | 4/2005 | Nordquist | 623/17.11 |
| 2005/0177245 A1 * | 8/2005 | Leatherbury et al. | 623/23.5 |
| 2005/0228498 A1 * | 10/2005 | Andres | 623/17.11 |
| 2005/0251268 A1 * | 11/2005 | Truncale | 623/23.63 |
| 2005/0278034 A1 | 12/2005 | Johnson et al. | |
| 2006/0020346 A1 * | 1/2006 | Hunter et al. | 623/23.51 |
| 2006/0173550 A1 | 8/2006 | Ragbir | |
| 2006/0224242 A1 * | 10/2006 | Swords et al. | 623/17.19 |
| 2006/0235542 A1 * | 10/2006 | Hodorek et al. | 623/23.51 |
| 2006/0241756 A1 * | 10/2006 | Fritz et al. | 623/14.12 |
| 2006/0293760 A1 * | 12/2006 | DeDeyne | 623/23.76 |
| 2007/0021838 A1 | 1/2007 | Dugas et al. | |
| 2007/0083268 A1 * | 4/2007 | Teoh et al. | 623/17.19 |
| 2007/0088443 A1 | 4/2007 | Hanssen et al. | |
| 2007/0093834 A1 * | 4/2007 | Stevens et al. | 606/69 |
| 2007/0135924 A1 | 6/2007 | Verhoogen | |
| 2007/0179607 A1 * | 8/2007 | Hodorek et al. | 623/14.12 |
| 2007/0213830 A1 * | 9/2007 | Ammann et al. | 623/20.32 |
| 2007/0233272 A1 * | 10/2007 | Boyce et al. | 623/23.63 |
| 2008/0133008 A1 * | 6/2008 | Truncale et al. | 623/14.12 |
| 2008/0188945 A1 * | 8/2008 | Boyce et al. | 623/23.61 |
| 2008/0195099 A1 * | 8/2008 | Minas | 606/70 |
| 2008/0249632 A1 * | 10/2008 | Stone et al. | 623/23.5 |
| 2008/0262616 A1 * | 10/2008 | McKay | 623/14.12 |
| 2009/0043398 A1 * | 2/2009 | Yakimicki et al. | 623/23.51 |
| 2009/0082770 A1 * | 3/2009 | Worner et al. | 606/60 |
| 2009/0149963 A1 | 6/2009 | Sekel | |
| 2009/0177203 A1 * | 7/2009 | Reiley | 606/87 |
| 2009/0306787 A1 | 12/2009 | Crabtree et al. | |
| 2010/0023130 A1 * | 1/2010 | Henry et al. | 623/17.18 |
| 2010/0047309 A1 * | 2/2010 | Lu et al. | 424/423 |
| 2010/0057197 A1 * | 3/2010 | Weber et al. | 623/1.42 |
| 2010/0114314 A1 | 5/2010 | Lomicka et al. | |
| 2010/0137990 A1 * | 6/2010 | Apatsidis et al. | 623/17.16 |
| 2010/0145452 A1 | 6/2010 | Blaylock et al. | |
| 2010/0241239 A1 | 9/2010 | Smith | |
| 2010/0292791 A1 * | 11/2010 | Lu et al. | 623/13.12 |
| 2011/0012280 A1 * | 1/2011 | Deslauriers et al. | 264/45.7 |
| 2011/0040334 A1 * | 2/2011 | Kaes et al. | 606/279 |
| 2011/0160870 A1 | 6/2011 | Baumgartner et al. | |
| 2011/0172798 A1 * | 7/2011 | Staiger et al. | 700/98 |
| 2011/0178604 A1 | 7/2011 | Porter | |
| 2011/0190887 A1 * | 8/2011 | Shapiro | 623/14.12 |
| 2011/0196503 A1 | 8/2011 | Anapliotis et al. | |
| 2011/0208189 A1 | 8/2011 | Faccioli et al. | |
| 2011/0213376 A1 * | 9/2011 | Maxson et al. | 606/88 |
| 2011/0238180 A1 * | 9/2011 | Fritz et al. | 623/14.12 |
| 2012/0232596 A1 * | 9/2012 | Ribeiro | 606/289 |
| 2012/0232656 A1 * | 9/2012 | Gedet et al. | 623/14.12 |
| 2012/0323324 A1 * | 12/2012 | Buskirk et al. | 623/13.14 |
| 2013/0030528 A1 * | 1/2013 | Chen et al. | 623/14.12 |
| 2013/0079877 A1 * | 3/2013 | Buma et al. | 623/14.12 |
| 2013/0090732 A1 * | 4/2013 | Duda et al. | 623/16.11 |
| 2013/0116788 A1 * | 5/2013 | Schwartz et al. | 623/14.12 |
| 2014/0045967 A1 * | 2/2014 | Thomas et al. | 523/115 |
| 2014/0172116 A1 * | 6/2014 | Maxson et al. | 623/23.53 |

OTHER PUBLICATIONS

Bio-Medicine; Pro Osteon Bone Graft Substitutes (2pgs).
Pro Osteon® 200R Bone Graft Substitute, Medcompare, Copyright 2003-2009, (2pgs).
Pro Osteon® 500R; Biomet, Copyright 2009 (1pg).
Pro Osteon® Biomet 200R (1pg).
The Natural Facts About Pro Osteon Implant 500, Interpore International (6pgs).

* cited by examiner

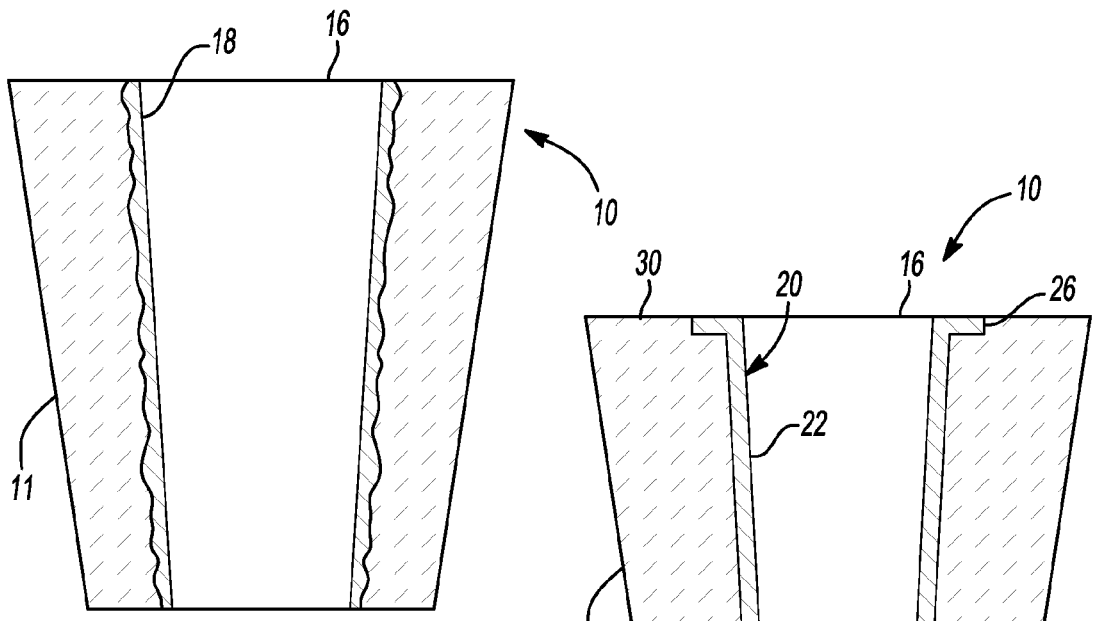
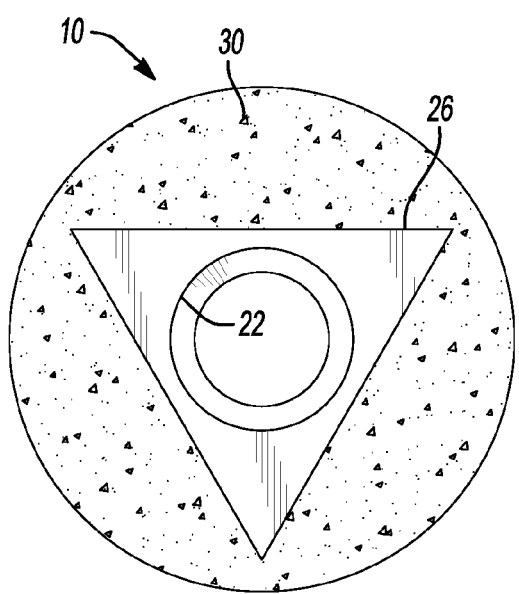
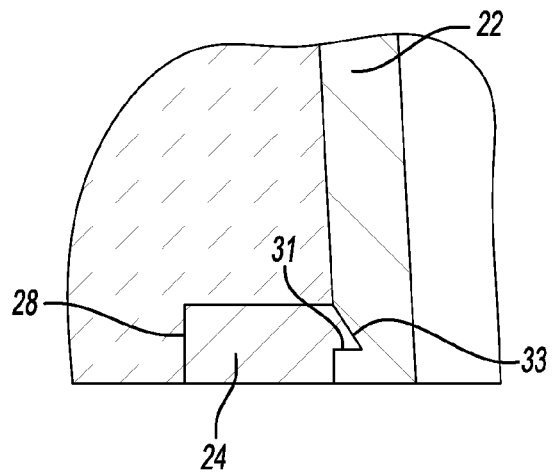

METHOD AND APPARATUS FOR AUGUMENTING BONE DEFECTS

CROSS-REFERENCE TO RELATED APPLICATIONS

This application is a divisional of U.S. application Ser. No. 12/708,309 filed Feb. 18, 2010. The entire disclosure of the above application is incorporated herein by reference.

FIELD

The present disclosure relates to methods and apparatus for augmenting bone defects.

BACKGROUND

This section provides background information related to the present disclosure and is not necessarily prior art.

Bone damage and/or bone loss can occur, for example, due to disease, trauma, and/or birth defects. Bone implants or augments can be used to repair such damaged bone. Bone augments are often manufactured from metal and have a permanent shape and size, thereby providing only limited restoration of bone stock. A bone augment that can be completely remodeled into bone over time and be modified intraoperatively would be desirable.

SUMMARY

This section provides a general summary of the disclosure, and is not a comprehensive disclosure of its full scope or all of its features.

The present teachings provide for a bone augment for repairing a bone defect. The bone augment includes a porous body and a metallic liner. The porous body defines a bore and is configured to be intraoperatively shaped to correspond to the bone defect. The metallic liner is injection molded within the bore such that portions of the liner interlock with pores of the porous body. The metallic liner is operable to mount an implant to the bone augment.

The present teachings also provide for a bone augment for repairing a bone defect that includes a porous body and a metallic liner. The porous body defines a bore and is configured to be intraoperatively shaped to correspond to the bone defect. The metallic liner is secured within the bore.

The present teachings also provide for a bone augment for repairing a bone defect that includes a bone engaging body and an exterior surface. The bone engaging body defines a plurality of pores. The body is configured to be intraoperatively shaped to correspond to the bone defect. An exterior surface of the bone engaging body includes a polymeric reinforcement member mounted thereto. The reinforcement member is operable to be intraoperatively shaped to correspond to the bone defect.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a cross-sectional view of the bone augment of FIG. 1B with a metallic sleeve mounted within a bore of the bone augment;

FIG. 5 is a cross-sectional view of the bone augment of FIG. 1B with a metallic insert mounted within the bore of the bone augment;

FIG. 5A is a top view of the bone augment of FIG. 5;

FIG. 5B illustrates the detail at area 5B of FIG. 5;

Corresponding reference numerals indicate corresponding parts throughout the several views of the drawings.

DETAILED DESCRIPTION

Figure 1A:
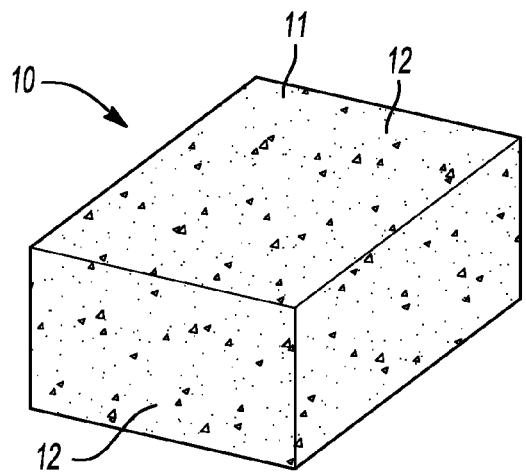
FIG. 1A is a perspective view of a bone augment according to the present teachings prior to being shaped to correspond to a particular bone defect.
Figure 1B:
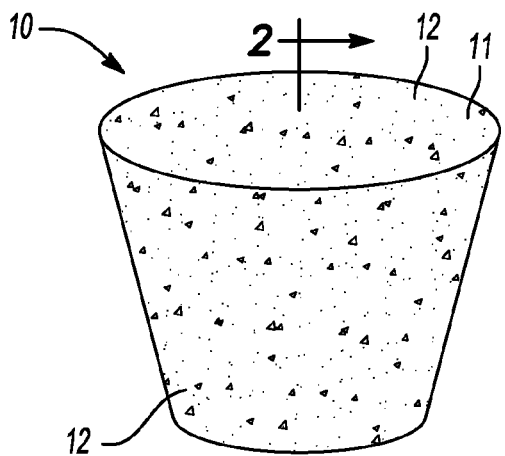
FIG. 1B is a perspective view of the bone augment of FIG. 1A after being shaped to correspond to a particular bone defect.

Example embodiments will now be described more fully with reference to the accompanying drawings.

A bone augment according to the present teachings is illustrated in FIGS. 1A-3 at reference numeral 10. The augment 10 includes a body 11 having a biocompatible construct that defines a plurality of pores 12, that can include a strengthening component 14. The augment 10 can be intraoperatively shaped as desired to fill a bone defect of most any size or shape, such as a defect in cancellous bone. The augment 10 can include a density similar to that of cancellous bone.

The augment 10 can be made of any suitable porous material, such as a ceramic or coral, which can be remodeled to bone. Suitable corals include coral hydrothermically converted to hydroxyapatite, such as any of the Pro Osteon® family of bone augments by Biomet of Warsaw, Ind., including Pro Osteon® 200R and 500R for example, which have pore sizes of about 200 and 500 microns respectively. Pro Osteon® is offered in various shapes and sizes, such as a square or rectangular block, as illustrated in FIG. 1A. Using a suitable cutting device, such as a scalpel, saw, or rongeurs, a block of Pro Osteon® can be shaped intraoperatively in any suitable manner, such as to provide a wedge-shaped augment 10 illustrated in FIG. 1B, in order to fill a bone defect of most any shape or size. Pro Osteon® is further described in U.S. Pat. No. 3,929,971 (issued Dec. 30, 1975 to Roy) and U.S. Pat. No. 4,976,736 (issued Dec. 11, 1990 to White et al.), which are hereby incorporated by reference. The porous construct of the augment 10 provides a matrix for new bone ingrowth to facilitate healing.

Figure 2:
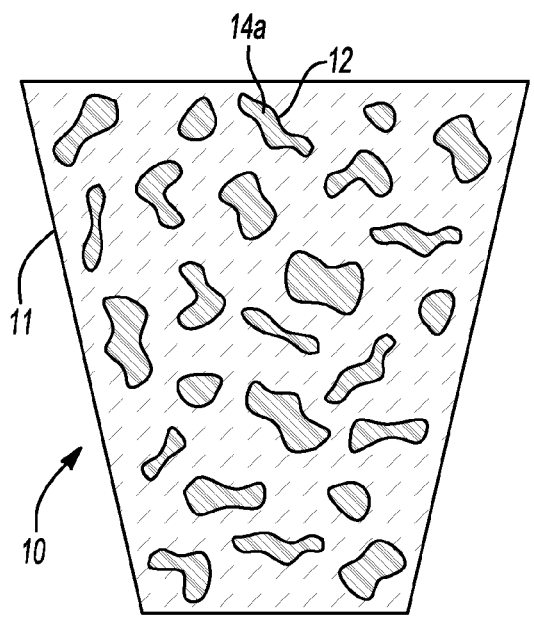
FIG. 2 is a cross-sectional view of the bone augment of FIG. 1B taken along line 2-2 and showing pores of the bone augment filled with a polymeric material.
Figure 3:
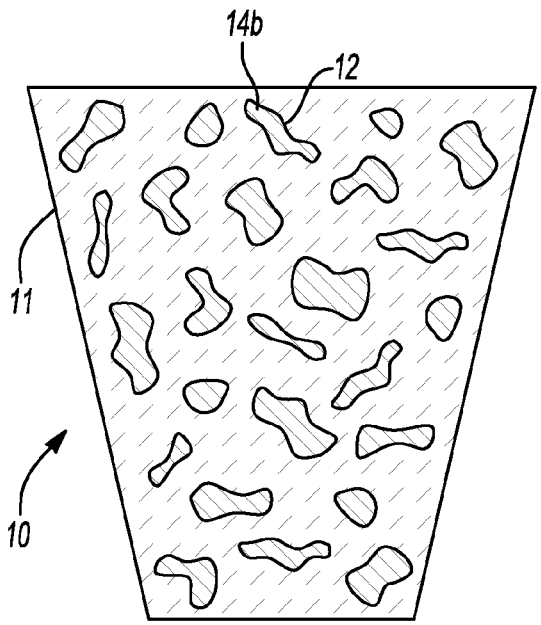
FIG. 3 is a cross-sectional view of the bone augment of FIG. 1B with the pores of the bone augment filled with a metallic material.

As illustrated in FIGS. 2 and 3, the augment 10 can include the strengthening component 14 within the pores 12 to enhance the mechanical strength of the augment 10. The strengthening component 14 can be inserted in the augment 10 in any suitable manner, such as by being injected into the pores 12. The strengthening component 14 can be provided such that it fills all of the pores 12, or only a portion of the pores 12. Upon implantation at a defect site, the body 11 resorbs and bone grows into voids previously occupied by the body 11, as well as into any of the pores 12 left unoccupied by the strengthening component.

The strengthening component 14 can include any suitable biocompatible component, such as a suitable polymer or non-metal 14A (FIG. 2), or a suitable metal 14B (FIG. 3). Suitable polymers and non-metals include one or more of the following: ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as described in U.S. Pat. No. 7,431,874 and all continuation applications and patents related thereto, which are incorporated herein by reference. An exemplary vitamin E stabilized HXLPE that may be used includes E-Poly™ offered by Biomet Orthopedics, Inc. of Warsaw, Ind. Suitable metals include, for example, CoCr, titanium, and combinations thereof. Use of the strengthening component 14 is optional.

With additional reference to FIG. 4, the body 11 of the augment 10 can define a bore 16 extending partially or entirely there through. The bore 16 can have any suitable size or shape. For example, the bore 16 can be tapered along its length as illustrated and have a size sufficient to accommodate a stem of a femoral implant therein. The bore 16 can be formed using any suitable cutting device, such as a suitable drill or mill.

The bore 16 can include any suitable liner operable to provide a mechanical connection with an implant, such as a femoral implant stem. The liner increases the strength of the augment 10 to facilitate support of the implant and prevent the augment from possibly fracturing. As illustrated in FIG. 4, the liner can include a tapered metallic sleeve 18 that is metal injection molded into the bore 16 to provide the metallic sleeve 18 with a unitary structure. During the injection molding process, portions of the metallic material enter the pores 12. Upon cooling, the metallic material provides a mechanical interlock with the pores 12 proximate to the bore 16. The tapered sleeve 18 provides a tapered connection with the stem of a femoral implant seated therein, such as a Morse taper lock.

Figure 5C:
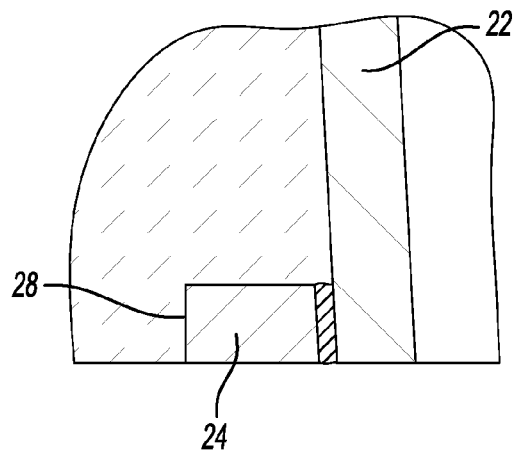
FIG. 5C illustrates an additional arrangement of the detail found at area 5B of FIG. 5.
Figure 5D:
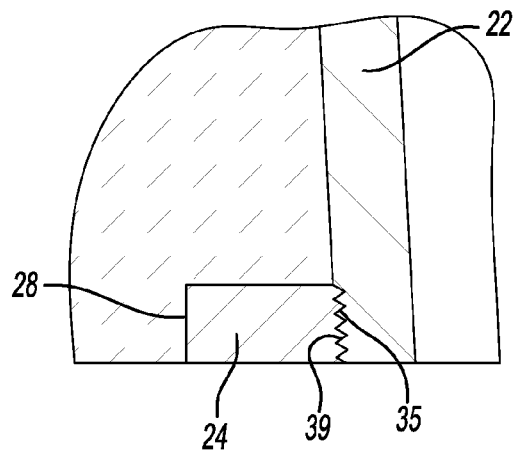
FIG. 5D illustrates another arrangement of the detail found at area 5B of FIG. 5.
Figure 5E:
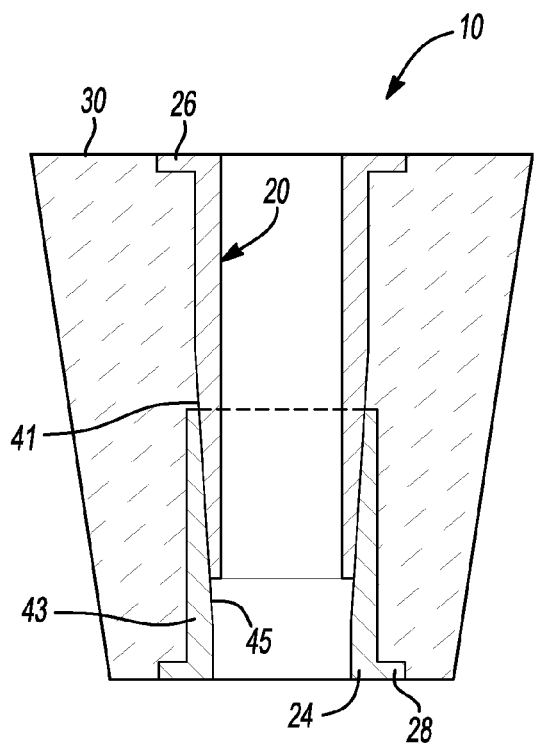
FIG. 5E is a cross-sectional view of the bone augment of FIG. 1B with an additional metallic insert mounted within the bore of the bone augment.

With additional reference to FIGS. 5 and 5A, the liner can include a modular metallic insert 20. The insert 20 includes a main body 22 and a cap 24. The main body 22 includes a first flange 26 and the cap 24 includes a second flange 28. The main body 22 and the cap 24 are positioned in the bore 16 such that the first flange 26 and the second flange 28 are proximate an exterior surface 30 of the augment 10. To accommodate the first flange 26 and the second flange 28, a portion of the exterior surface 30 can be cut out using a suitable cutting device, such as a scalpel, knife, or rongeurs, to permit the first flange 26 and the second flange 28 to be positioned coplanar with the exterior surface 30. In the alternative, the portion of the exterior surface 30 that is cut out can be made in a manufacturing environment, such as with a mill. The first flange 26 and the second flange 28 can also be positioned such that they protrude slightly beyond the exterior surface 30.

The first flange 26 and the second flange 28 can be annular flanges or have any suitable shape to restrict rotation of the insert 20 within the bore 16, such as triangular, square, or hexagonal. The shape of the flanges 26 and 28 can be independent of the shape of the bore 16. For example, FIG. 5A illustrates the first flange 26 having a triangular shape and the main body 22 of the insert 20 having a cylindrical shape. A suitable adhesive can also be provided between the insert 20 and the portion of the body 11 defining the bore 16 to restrict rotation of the insert 20 and retain the insert 20 within the bore 16. Absent the insert 20, friction between the insert 20 and the portion of the body 11 defining the bore 16 can also assist in retaining the insert 20 within the bore 16 and restrict rotation of the insert 20.

As illustrated in FIGS. 5 and 5B, the cap 24 includes a tab 31 that is configured to mate with a recess 33 at an exterior surface of the insert 20 to secure the cap 24 to the main body 22. Thus, after the main body 22 is inserted in the bore 16, the cap 24 is mounted thereto by snapping the tab 31 into the recess 33. The tab 31 and the recess 33 can be annular or there can be multiple tabs 31 and recesses 33 spaced about the cap 24 and main body 22 respectively. Further, the illustrated configuration can be reversed such that the tab 31 can be provided on the main body 22 and the recess 33 is provided in the cap 24.

The cap 24 can be mounted to the main body 22 in any suitable manner. For example and with reference to FIG. 5C, the cap 24 can be welded to the main body 22 using a suitable welding device. Further, and with additional reference to FIG. 5D, the main body can include threads 35 that cooperate with threads 39 to allow the cap 24 to be screwed into engagement with the main body 22. Also and with reference to FIG. 5E, the main body 22 can be provided with a first elongated tapered outer surface 41 and the cap 24 can be provided with a stem 43 having a second elongated tapered outer surface 45. The first tapered surface 41 and the second tapered surface 45 are angled such that a Morse taper lock is formed therebetween when the surfaces 41 and 45 are pressed together.

Figure 6:
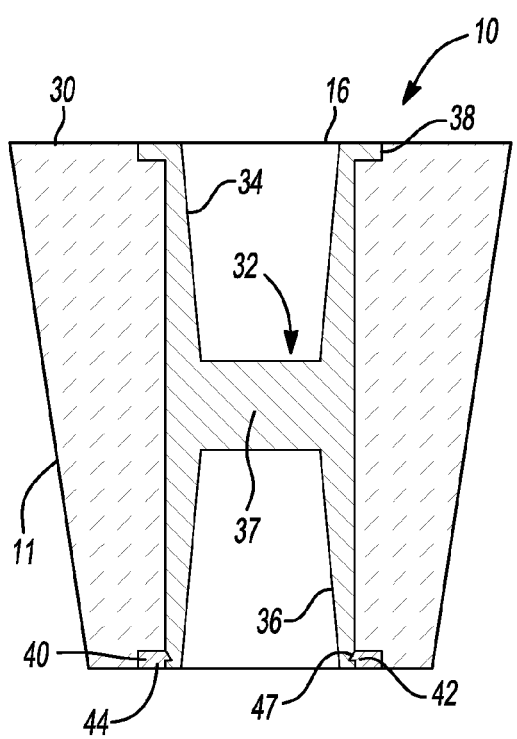
FIG. 6 is a cross-sectional view of the bone augment of FIG. 1B with a taper base mounted within the bore of the bone augment.

With additional reference to FIG. 6, the liner can include a taper base 32 having a first taper 34 and a second taper 36 with a support portion 37 therebetween to provide additional strength and support to the insert 20. The first taper 34 is of any suitable size or shape to provide a Morse taper connection with a suitable implant component, such as a femoral neck for supporting a femoral head. The second taper 36 is of any suitable size or shape to provide a Morse taper connection with another suitable implant component, such as a femoral stem. While the taper base 32 is illustrated as including taper connections 34 and 36, the taper base 32 can include any other suitable attachment feature in place of, or in addition to, the taper connections 34 and 36.

The taper base 32 includes a flange 38 at an end thereof that abuts the exterior surface 30 of the augment 10 when the taper base 32 is seated within the bore 16. A cap 40 interlocks with the taper base 32 in any suitable manner, such as through a snap-fit connection between a tab 42 extending from the cap 40 and a recess 47 in the taper base 32. Further, any of the other connection mechanisms described herein can be used, such as those described in FIGS. 5B-5E.

The cap 40 includes a flange 44 that abuts the exterior surface of the augment 10 to secure the taper base 32 within the bore 16 to restrict axial movement of the taper base 32 within the bore 16. The flanges 38 and 44 are positioned proximate to the exterior surface 30 of the augment 10. To accommodate the flanges 38 and 44, a portion of the exterior surface 30 can be cut out using a suitable cutting device, such as a scalpel, knife, or rongeurs, to permit the flanges 38 and 44 to be positioned coplanar with the exterior surface 30. In the alternative, the portion of the exterior surface 30 that is cut out can be made in a manufacturing environment, such as with a mill. The flanges 38 and 44 can also be positioned such that they protrude slightly beyond the exterior surface 30. The flanges 38 and 44 can be annular flanges or have any suitable shape to restrict rotation of the taper base 32 within the bore 16, such as triangular similar to the shape of the flange 26 of FIG. 5A, square, or hexagonal.

Figure 7:
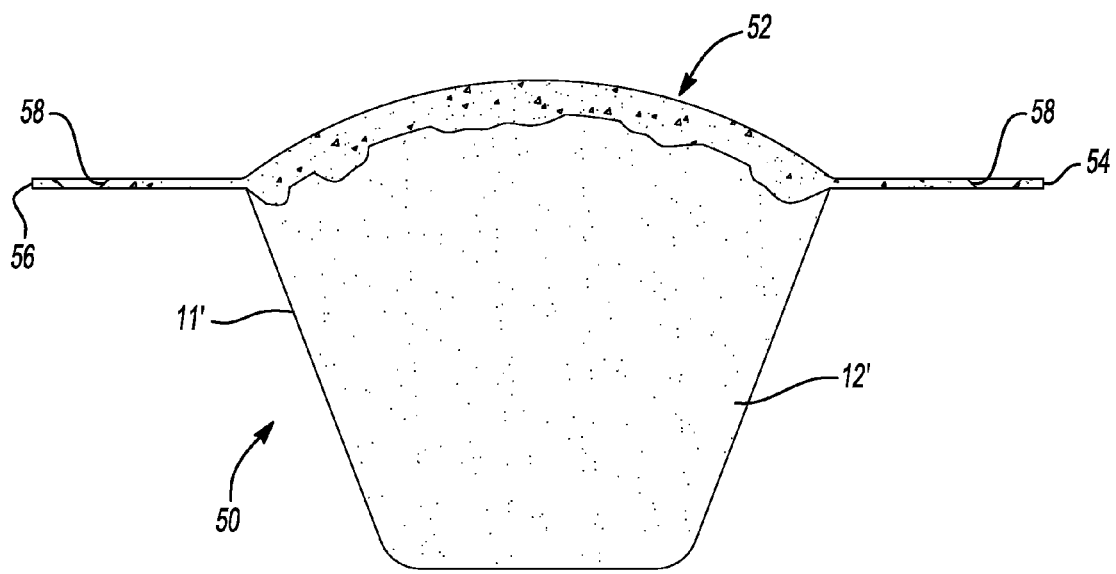
FIG. 7 is a cross-sectional view of a bone augment according to an additional aspect of the present teachings, the bone augment including a reinforcement member mounted thereto.

With additional reference to FIG. 7, another augment according to the present teachings is illustrated at reference numeral 50. The augment 50 can include the same materials and composition as described herein with respect to the augment 10. Thus, the description of the materials and composition of the augment 10 also serves as a description of the augment 50 and need not be repeated. Like the augment 10, the augment 50 includes a body that defines a plurality of pores. The body and pores of the augment 50 are similar to the body 11 pores 12 of the augment 10 and thus are designated with the reference numerals 11' and 12' respectively. The body 11' can replace cancellous bone, as described below.

The augment 50 also includes a reinforcement member 52. The reinforcement member 52 includes a first projection 54 and a second projection 56, each projection 54 and 56 includes an aperture 58 capable of receiving a suitable fastening device, such as a screw 60. The reinforcement member 52 can replace cortical bone, as described further below, and includes a density similar to cortical bone. The reinforcement member 52 can include any suitable biocompatible material, such as one or more metallic or polymeric materials.

Suitable polymers or non-metals include one or more of the following: ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as described in U.S. Pat. No. 7,431,874 and all continuation applications and patents related thereto, which are incorporated herein by reference. An exemplary vitamin E stabilized HXLPE that may be used includes E-Poly or E1™ offered by Biomet of Warsaw, Ind. Suitable metals include, for example, CoCr, titanium, and combinations thereof.

The projections 54 and 56 can be deformed in any suitable manner to match the morphology of a repair site. For example, the projections 54 and 56 can be bent with a suitable instrument (such as pliers or a roll bender, for example), can be pressed into a mold of the implant site, and can be machined during manufacturing to correspond a specific patient's morphology.

The reinforcement member 52 can be mounted to the augment 50 in any suitable matter, such as with injection molding or compression molding. With both injection molding and compression molding, portions of the reinforcement member 52 enter a portion of the pores 12' to provide a mechanical interlock with the pores 12'. As with the augment 50, the reinforcement member 52 can be machined in order to fit a particular defect site. As further discussed herein, the augment with the reinforcement member 52 mounted thereto can be used to fill an uncontained defect, such as at a peripheral portion of a tibia upper extremity, because the reinforcement member 52 can retain the augment 50 in an uncontained defect through cooperation between the screws 60 and surrounding bone.

Figure 8:
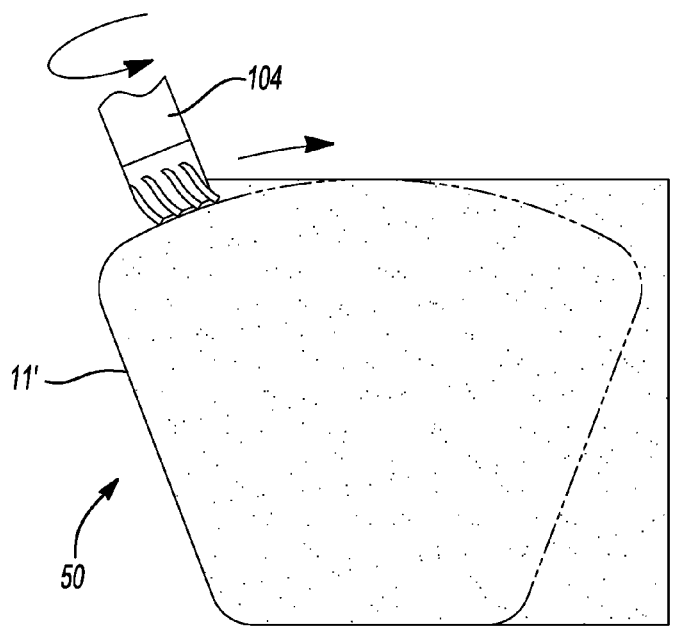
FIG. 8 is a side view of the bone augment of FIG. 1 being intraoperatively shaped to fit a bone defect.

As illustrated in FIG. 8, the augment 50 can be intraoperatively shaped to accommodate a defect. Both the body 11' and the reinforcement member 52 can be shaped. To shape the body 11', a cutting device 104, such as a scalpel, saw, or rongeurs, for example, can be used. To shape the reinforcement member 52, a bur, saw, or rongeurs, for example, can be used.

Figure 9:
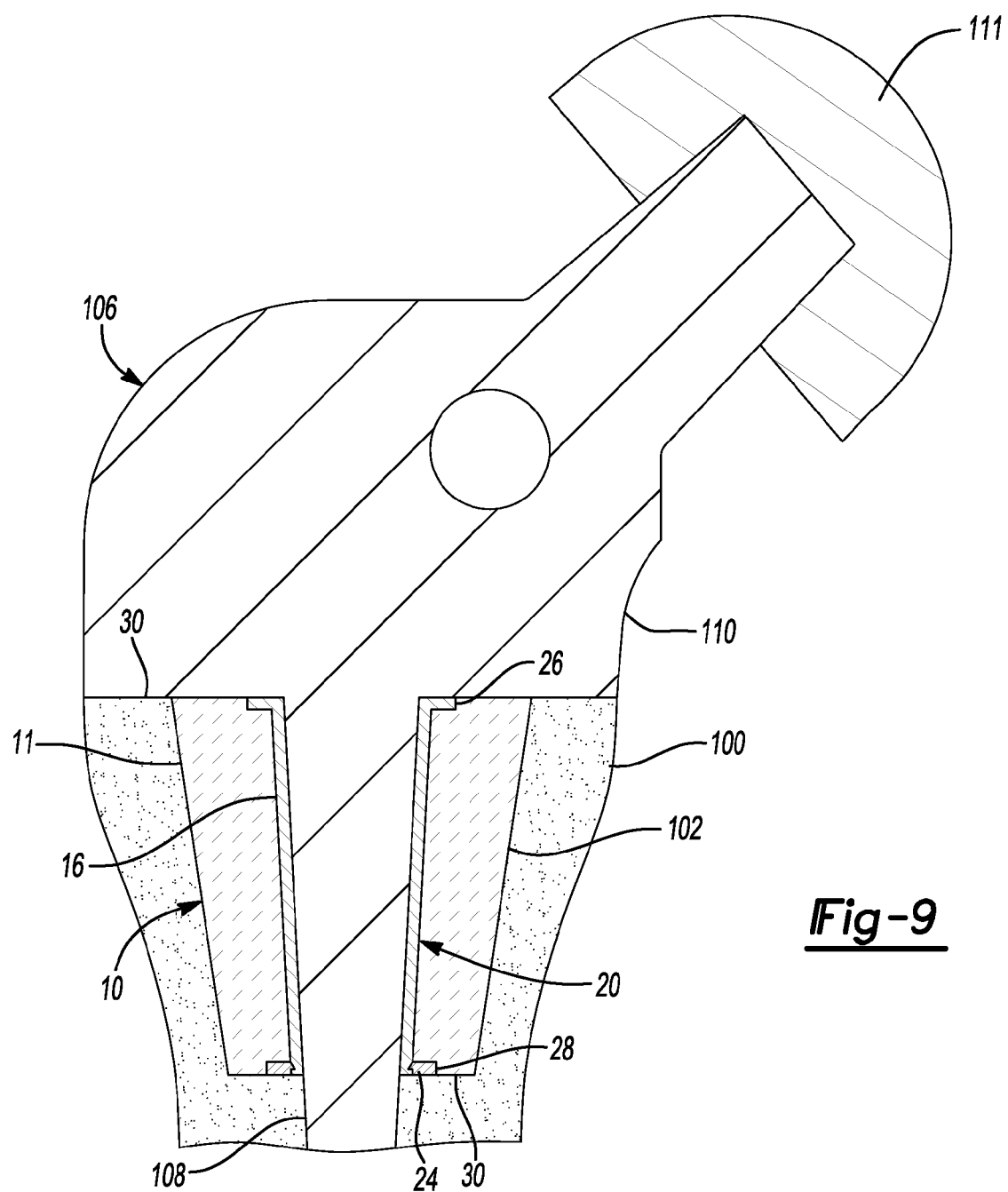
FIG. 9 is a cross-sectional view of the bone augment of FIG. 5 seated within a defect site of a femur to support a femoral implant.

With additional reference to FIG. 9, use of the porous augment 10 in a proximal portion of a femur 100 to fill a defect 102 during a femoral joint replacement is illustrated. The augment 10 includes the bore 16 and the insert 20 mounted therein. The bore 16 is formed therein with a suitable cutting device, such as a suitable drill or mill.

To shape the body 11, a suitable cutting device, such as a scalpel, saw, or rongeurs, for example, can be used. The shaped augment 10 is secured at the defect site 102 in any suitable manner, such as with a press-fit or suitable fastener, to fill damaged cancellous bone. The composition of the augment 10, particularly Pro Osteon®, permits insertion of a fastener into the augment 10 without pre-drilling. Any suitable implant, such as a femoral implant 106 having a stem 108 and a neck 110 supporting a head 111, can be attached to the augment 10 for support. As illustrated, the stem 108 is inserted into the bore 16 to mate with the metallic insert 20, which secures the stem 108 with a press-fit and/or a Morse taper. During the healing process bone grows into the pores 12 of the augment 10 and the augment 10 is remodeled into the femur 100, except for the metallic insert 20.

The insert 20 is optional. When the insert 20 is not used, the stem 108, or any suitable implant, can be secured within the bore 16 with a suitable fastening device or material, such as poly methyl methacrylate ("PMMA") bone cement.

Figure 10:
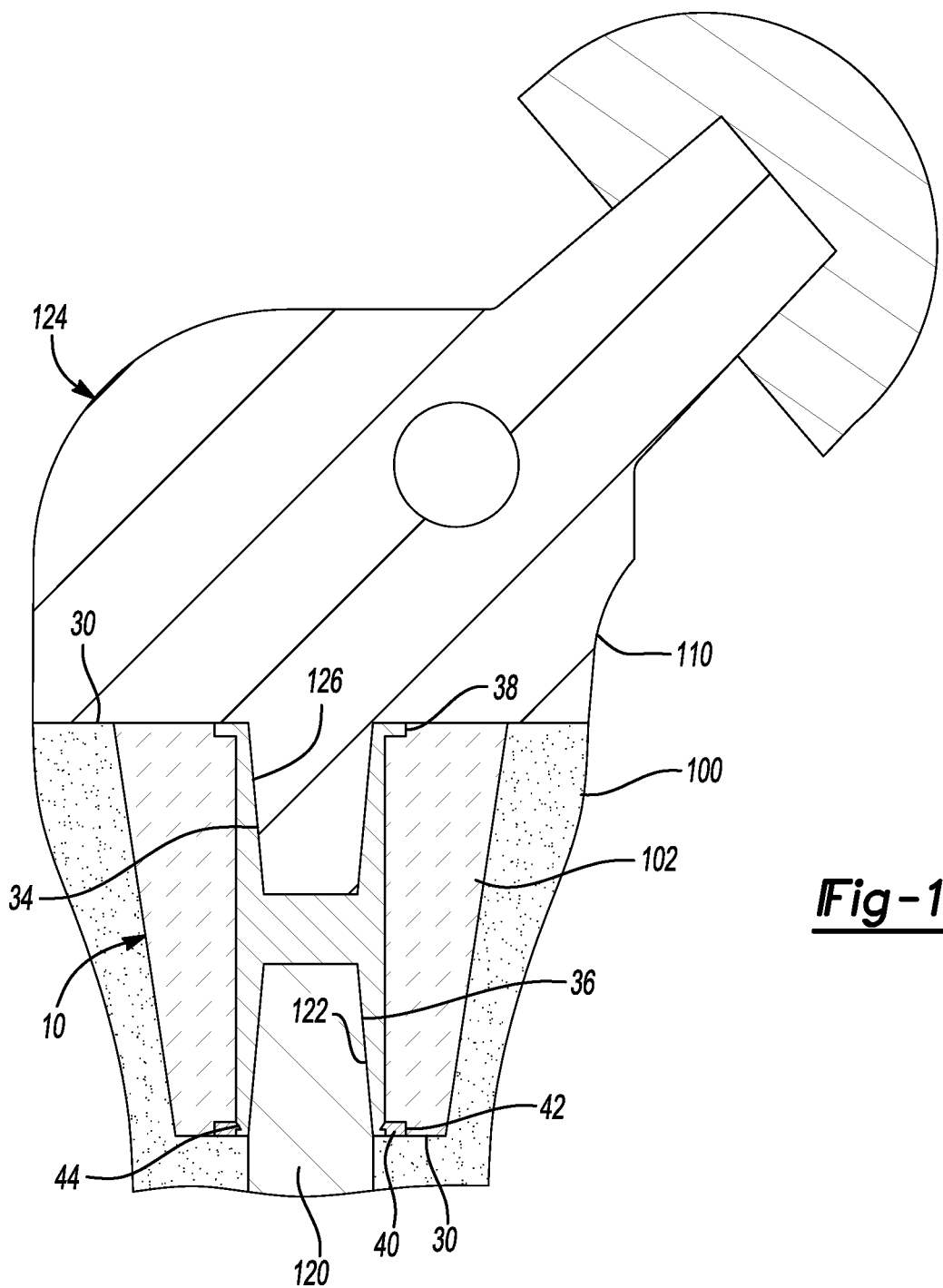
FIG. 10 is a cross-sectional view of the bone augment of FIG. 6 mounted within a defect site of a femur to support a femoral stem implant and a femoral head implant.

With additional reference to FIG. 10, implantation of the augment 10 including the taper base 32 is illustrated. As described previously, the augment 10 is intraoperatively shaped to fill the defect 102 and then secured in the defect 102 in any suitable manner, such as with a press-fit or suitable fastener, to fill damaged cancellous bone. The second taper 36 of the taper base 32 is mounted to a suitable implant, such as a femoral stem implant 120. A taper connection surface 122 of the stem implant 120 is mated with the second taper 36 of the taper base 32 to secure the femoral stem implant 120 to the taper base 32 with a Morse taper. A femoral neck implant 124 having a taper connection 126 is mounted to the taper base 32 through cooperation between the taper connection 126 and the first taper 34 of the taper base 32. During healing the augment 10 is remodeled into the femur 100, except for the taper base 32. As illustrated, the taper connection surface 122 provides the male end of the Morse taper and the second taper 36 provides the female end, but this configuration can be reversed.

Figure 11A:
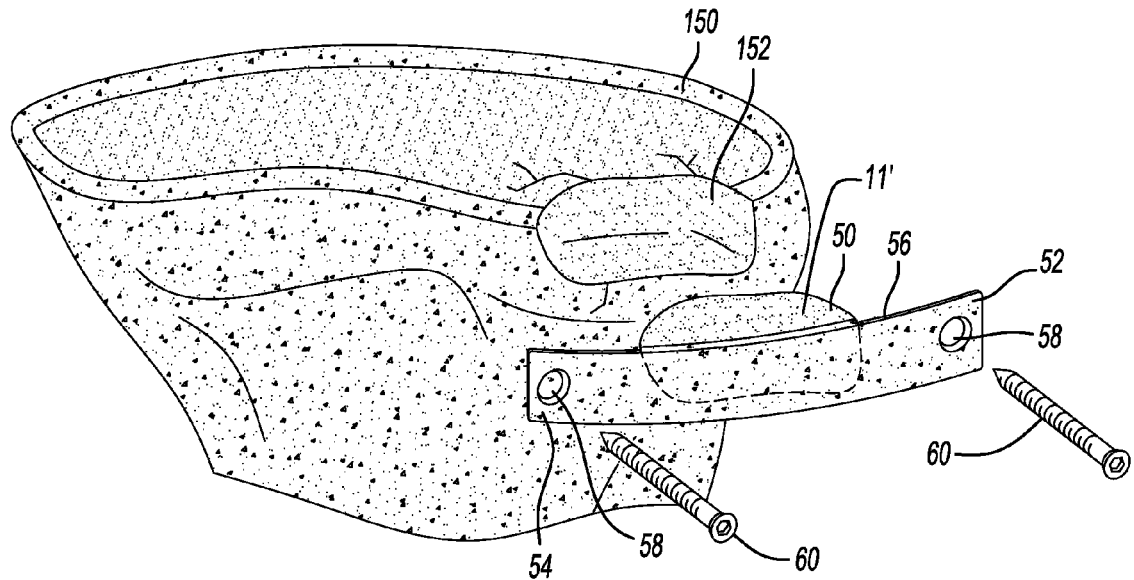
FIG. 11A is a perspective view of the bone augment of FIG. 7 being implanted in a defect site of a tibia bone.
Figure 11B:
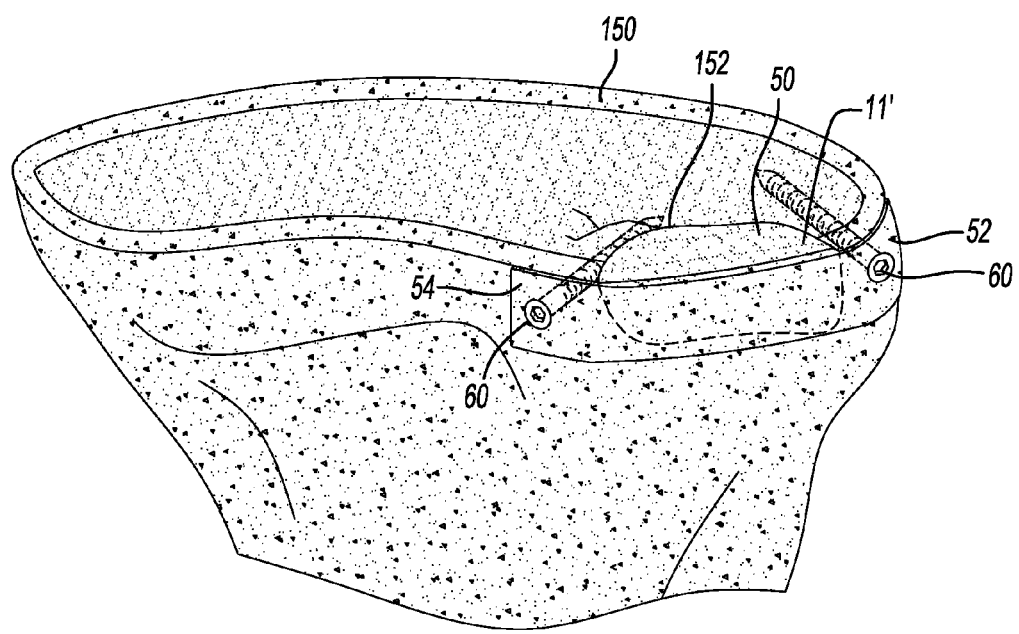
FIG. 11B is a perspective view of the bone augment of FIG. 7 implanted within the defect site of the tibia bone.
Figure 12:
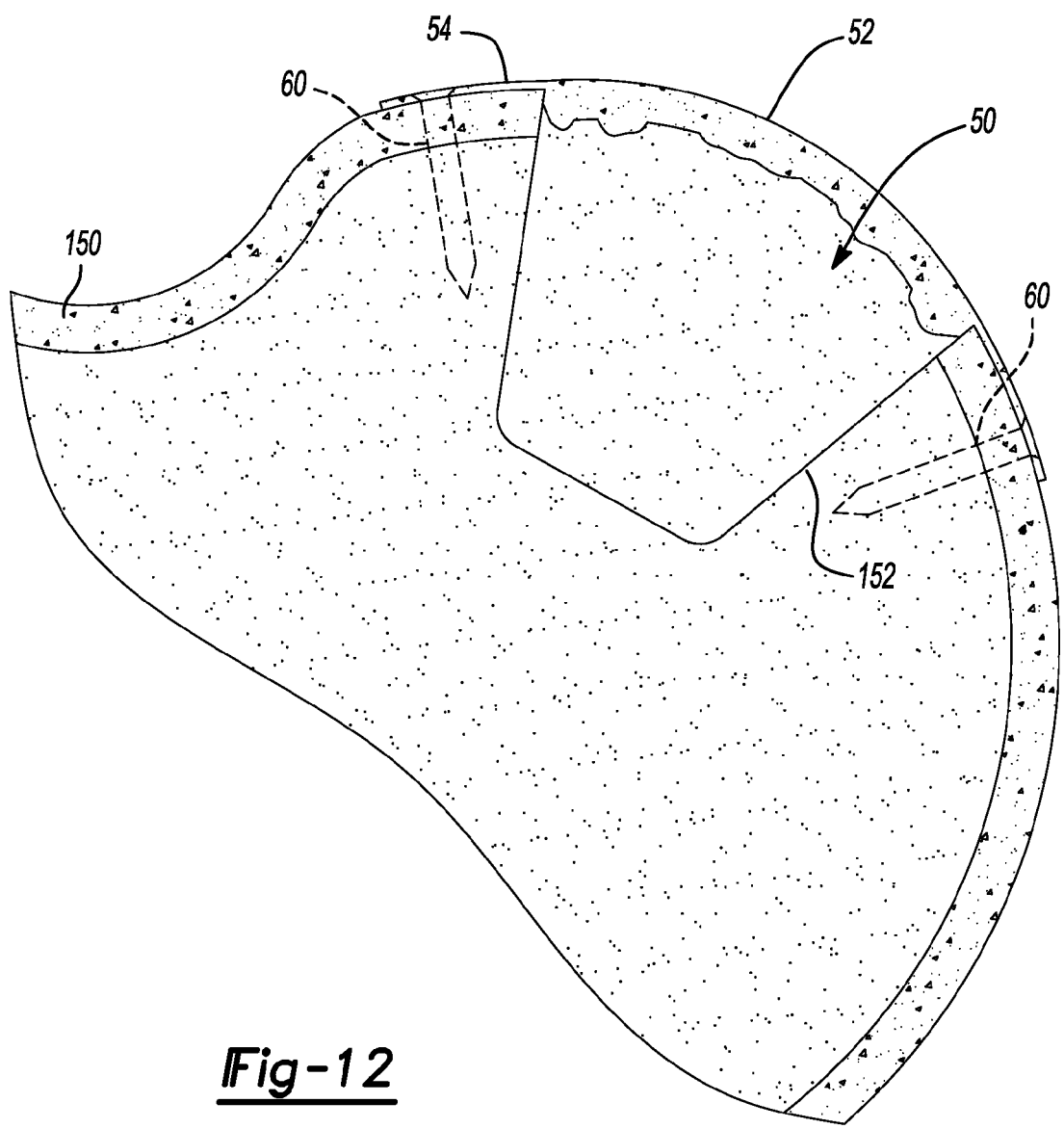
FIG. 12 is a top view of the bone augment of FIG. 7 implanted within the defect site of the tibia bone.

With reference to FIGS. 11A, 11B, and 12, use of the porous augment 50 at an upper extremity of a tibia 150 to fill a defect 152 is illustrated. The augment 50 includes the reinforcement member 52 mounted thereto.

The augment 50 and reinforcement member 52 can each be intraoperatively shaped to accommodate the uncontained defect 152 using a suitable cutting device. To shape the body 11' the cutting device 104, such as a scalpel, saw, or rongeurs, for example, can be used. To shape the reinforcement member 52, a bur, saw, or rongeurs, for example, can be used. The shaped augment 50 is secured at the defect site 152 with the screws 60, which extend through the projections 54 and 56 and into an area of the tibia 150 proximate to the defect 152 having bone of sufficient rigidity to retain the screws 60, such as cortical bone. During the healing process, cancellous bone is permitted to grow into the pores 12' of the augment 50 and the augment 50 is remodeled into the tibia 150, except for the polymeric reinforcement member 52, the rigidity of which serves to replace the missing cortical bone. Thus, the augment 50 is positioned such that the body 11' provides a bone engaging surface and the reinforcement 52 provides a exterior surface.

Use of the augments 10 and 50 in the femur 100 and the tibia 150 is for exemplary purposes only. The bone augments 10 and 50 can be used to repair any suitable defect in suitable bone. To accommodate use of the augments 10 and 50 in bones of various different sizes, various sized augments 10 and 50 can be provided.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A bone augment for repairing a bone defect present in a single bone comprising:
    a bone-engaging body defining a plurality of pores, the body configured to be intraoperatively shaped to correspond to the bone defect present in the single bone; and
    a polymeric reinforcement member having an inner surface and an outer surface, the inner surface having a first part and a second part, wherein the first part of the inner surface of the polymeric reinforcement member is mounted on an exterior surface of the bone-engaging body, the second part of the inner surface of the reinforcement member is configured to be in contact with an outer bone surface proximate to the bone defect, and the reinforcement member is configured to be intraoperatively deformed to correspond to the bone defect present in the single bone and the outer bone surface proximate to the bone defect;
    wherein:
    the first part of the inner surface of the polymeric reinforcement member is molded to the exterior surface such that portions of the reinforcement member are mechanically interlocked with the pores; and
    the body includes a density that approximates a density of cancellous bone and the polymeric reinforcement member includes a density that approximates a density of cortical bone.

2. The bone augment of claim 1, the second part further comprising a projection extending from the polymeric reinforcement member, the projection including an aperture configured to receive a fastener to secure the bone augment to bone proximate to the bone defect.

3. The bone augment of claim 1, wherein the body includes at least one of a ceramic and Pro Osteon® and the polymeric reinforcement member includes polyether ether ketone.

4. The bone augment of claim 1, wherein the bone augment is configured to repair an uncontained bone defect with the body replacing cancellous bone and the polymeric reinforcement member replacing cortical bone.

5. The bone augment of claim 1, the second part further comprising first and second projections extending from opposite sides the polymeric reinforcement member, each of the first and second projections including an aperture configured to receive a corresponding fastener to secure the bone augment to the single bone proximate to the bone defect present in the single bone.

6. The bone augment of claim 5, wherein each of the first and second projections is deformable to match the morphology proximate to the bone defect.

7. The bone augment of claim 5, wherein each of the first and second projections can be machined during manufacturing to match a specific patient's morphology.

8. The bone augment of claim 5, wherein each of the first and second projections can be pressed into a mold of a corresponding implant site of a specific patient.

9. The bone augment of claim 1, wherein the reinforcement member is mounted on the body by injection or compression molding.

10. A bone augment for repairing a bone defect comprising:
    a bone-engaging body defining a plurality of pores, the body configured to be intraoperatively shaped to correspond to the bone defect entirely defined at an upper extremity of a tibia; and
    a polymeric reinforcement member having an inner surface and an outer surface, the inner surface having a first part and a second part, wherein the first part of the inner surface of the polymeric reinforcement member is mounted on an exterior surface of the bone-engaging body and the second part of the inner surface of the polymeric reinforcement member having first and second extensions corresponding to opposite sides of the defect entirely defined at the upper extremity of the tibia, and the reinforcement member configured to be intraoperatively deformed to correspond to the bone defect entirely defined at the upper extremity of the tibia with the first and second extensions configured to be deformed to correspond to an outer bone surface proximate to the bone defect;
    wherein:
    the first part of the inner surface of the polymeric reinforcement member is molded to the exterior surface such that portions of the reinforcement member are mechanically interlocked with the pores; and
    the body includes a density that approximates a density of cancellous bone and the polymeric reinforcement member includes a density that approximates a density of cortical bone.

11. The bone augment of claim 10, wherein each of the first and second projections is deformable to match a patient's morphology proximate to the bone defect.

12. The bone augment of claim 10, wherein each of the first and second projections can be machined during manufacturing to match a specific patient's morphology.

13. The bone augment of claim 10, wherein each of the first and second extensions include an aperture configured to receive a corresponding fastener to secure the bone augment to a single bone proximate to the bone defect entirely defined at the upper extremity of the tibia.

14. The bone augment of claim 10, wherein the body includes at least one of a ceramic and Pro Ostean® and the polymeric reinforcement member includes polyether ether ketone.

15. The bone augment of claim 10, wherein the bone augment is configured to repair the bone defect when the bone defect is an uncontained bone defect with the body replacing cancellous bone and the polymeric reinforcement member replacing cortical bone.

16. A method for repairing a bone defect comprising:
   molding an inner surface of a polymeric reinforcement member to an exterior surface of a porous body at a first part of the inner surface of the polymeric reinforcement member such that portions of the reinforcement member are mechanically interlocked with pores of the porous body;
   inserting the porous body into a bone defect entirely defined by a single bone, the porous body shaped to correspond to the bone defect entirely defined by the single bone;
   deforming first and second extensions of a second part of the inner surface of the polymeric reinforcement member of the bone augment to match the inner surface at the second part of the polymeric reinforcement member with an outer surface of the single bone on opposite sides of the bone defect; and
   fastening the first and second extensions of the second part of the inner surface of the polymeric reinforcement member to the single bone on opposite sides of the bone defect entirely defined by the single bone;
   wherein the body includes a density that approximates density of cancellous bone and the polymeric reinforcement member includes a density that approximates density of cortical bone.

17. The method of claim 16, further comprising bending the first and second extensions to match a patient morphology of the single bone around the bone defect entirely defined by the single bone.

18. The method of claim 16, wherein the bone augment is configured for a bone defect entirely defined at an upper extremity of a tibia.

19. The method of claim 16, further comprising inserting the porous body into an uncontained bone defect entirely defined by the single bone such that the porous body replaces cancellous bone and the polymeric reinforcement member replaces cortical bone.

* * * * *